United States Patent
Stinson (10) Patent No.: US 8,388,676 B2
(45) Date of Patent: Mar. 5, 2013

(54) DISINTEGRATING STENT AND METHOD OF MAKING SAME

(75) Inventor: Jonathan S. Stinson, Plymouth, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1119 days.

(21) Appl. No.: 10/742,943

(22) Filed: Dec. 23, 2003

(65) Prior Publication Data

US 2004/0138738 A1 Jul. 15, 2004

Related U.S. Application Data

(62) Division of application No. 09/592,413, filed on Jun. 13, 2000, now abandoned.

(51) Int. Cl.
*A61F 2/06* (2006.01)
(52) U.S. Cl. ...................................................... 623/1.38
(58) Field of Classification Search ................ 623/1.38, 623/1.15, 1.11–1.13
See application file for complete search history.

(56) References Cited

U.S. PATENT DOCUMENTS

| | | | |
|---|---|---|---|
| 4,655,771 A | 4/1987 | Wallsten | |
| 4,954,126 A | 9/1990 | Wallsten | |
| 5,026,377 A | 6/1991 | Burton et al. | |
| 5,061,275 A | 10/1991 | Wallsten et al. | |
| 5,078,736 A * | 1/1992 | Behl | 623/1.15 |
| 5,201,757 A | 4/1993 | Heyn et al. | |
| 5,500,013 A | 3/1996 | Buscemi et al. | |
| 5,628,787 A | 5/1997 | Mayer | |
| 5,630,840 A | 5/1997 | Mayer | |
| 5,645,559 A | 7/1997 | Hachtman et al. | |
| 5,888,201 A | 3/1999 | Stinson et al. | |
| 5,957,975 A * | 9/1999 | Lafont et al. | 623/1.16 |
| 5,980,564 A | 11/1999 | Stinson | |
| 5,985,307 A | 11/1999 | Hanson et al. | |
| 6,015,422 A | 1/2000 | Kerr | |
| 6,042,578 A | 3/2000 | Dinh et al. | |
| 6,156,064 A * | 12/2000 | Chouinard | 623/1.44 |
| 6,174,330 B1 | 1/2001 | Stinson | |
| 6,228,111 B1 | 5/2001 | Tormala et al. | |
| 6,245,103 B1 | 6/2001 | Stinson | |
| 6,485,510 B1 * | 11/2002 | Camrud et al. | 623/1.16 |
| 6,500,204 B1 * | 12/2002 | Igaki | 623/1.18 |
| 6,613,079 B1 * | 9/2003 | Wolinsky et al. | 623/1.15 |
| 7,018,401 B1 * | 3/2006 | Hyodoh et al. | 623/1.12 |

OTHER PUBLICATIONS

International Preliminary Examination Report, PCT/US01/40940, dated Apr. 30, 2003 at wipo.int.

* cited by examiner

*Primary Examiner* — Katherine Dowe
(74) *Attorney, Agent, or Firm* — Vidas, Arrett & Steinkraus, P.A.

(57) ABSTRACT

A temporary stent endoprosthesis that does not require an interventional procedure for removal. The disintegrating stent is preferably made from a bioabsorbable polymer, such as by braiding polymer monofilaments into a tubular mesh shape, and the polymer has fracture initiation sites within it that promotes the disintegration of the stent into small pieces that are harmlessly transported out of the body by the vessel contents. Fracture initiation sites may be created by controlling the heterogenous structure of amorphous and crystalline regions, by introducing internal or surface fracture initiation sites, or use of multiple strands with small section size.

29 Claims, 11 Drawing Sheets

DISINTEGRATING STENT AND METHOD OF MAKING SAME

CROSS REFERENCE TO RELATED APPLICATIONS

This application is a divisional of application Ser. No. 09/592,413, filed Jun. 13, 2000 now abandoned.

BACKGROUND OF THE INVENTION

1. Field of the Invention

The present invention relates generally to implantable temporary medical prostheses that do not require interventional procedures for removal. In particular, the present invention is a disintegrating implantable medical prosthesis that disintegrates into small pieces that are harmlessly transported out of the body by normal body function.

2. Related Technology

Medical prostheses frequently referred to as stents are well known and commercially available. They are, for example, disclosed generally in the Wallsten U.S. Pat. No. 4,655,771, the Wallsten et al. U.S. Pat. No. 5,061,275 and in Hachtmann et al., U.S. Pat. No. 5,645,559. Devices are used within body vessels of humans for a variety of medical applications. Examples include intravascular stents for treating stenoses, stents for maintaining openings in the urinary, biliary, tracheobronchial, esophageal, and renal tracts, and vena cava filters.

A delivery device which retains the stent in its compressed state is used to deliver the stent to a treatment site through vessels in the body. The flexible nature and reduced radius of the compressed stent enables it to be delivered through relatively small and curved vessels. In percutaneous transluminal angioplasty, an implantable endoprosthesis is introduced through a small percutaneous puncture site, airway, or port and is passed through various body vessels to the treatment site. In endoscopy, the delivery device is passed through the instrument channel of the scope. After the stent is positioned at the treatment site, the delivery device is actuated to release the stent. Following release of the stent, the stent is allowed to self-expand within the body vessel, in the case of self-expanding stents, or alternatively, a balloon is used to expand the stent. The delivery device is then detached from the stent and removed from the patient. The stent remains in the vessel at the treatment site as an implant.

Stents must exhibit a relatively high degree of biocompatibility since they are implanted in the body. An endoprosthesis may be delivered into a body lumen on or within a surgical delivery system such as delivery devices shown in U.S. Pat. Nos. 4,954,126 and 5,026,377. Suitable materials for use with such delivery devices are described in U.S. patent application Ser. No. 08/833,639, filed Apr. 18, 1997.

Commonly used materials for known stent filaments include Elgiloy® and Phynox® metal spring alloys. Other metallic materials that can be used for stent filaments are 316 stainless steel, MP35N alloy, and superelastic Nitinol nickel-titanium. Another stent, available from Schneider (USA) Inc. of Minneapolis, Minn., has a radiopaque clad composite structure such as shown in U.S. Pat. No. 5,630,840 to Mayer. Stents can also be made of a Titanium alloy as described in U.S. Pat. No. 5,888,201.

Bioabsorbable stents have also been proposed, for example in U.S. patent application Ser. No. 08/904,467 entitled Bioabsorbable Self-Expanding Stent, filed Aug. 1, 1997, and commonly assigned to the assignee of this application. Such bioabsorbable stents may be formed, for example, from a number of resilient filaments which are helically wound and interwoven in a braided configuration. Such stents assume a substantially tubular form in their unloaded or expanded state when they are not subjected to external forces. When subjected to inwardly directed radial forces, the bioabsorbable stents are forced into a reduced-radius and extended-length loaded or compressed state. Bioabsorbable stents are generally characterized by a longitudinal shortening upon radial expansion.

Bioabsorbable implantable endoprostheses such as stents, stent-grafts, grafts, filters, occlusive devices, and valves may be made of poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymers materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

The implantation of an intraluminal stent generally causes a generally reduced amount of acute and chronic trauma to the luminal wall while performing its function. Stents that apply a gentle radial force against the wall and that are compliant and flexible with lumen movements are generally used in diseased, weakened, or brittle lumens. Such stents are generally capable of withstanding radially occlusive pressure from tumors, plaque, and luminal recoil and remodeling.

There remains a continuing need for stents with particular characteristics for use in various medical indications. Stents are needed for implantation in an ever growing list of vessels in the body. Different physiological environments are encountered and it is recognized that there is no universally acceptable set of stent characteristics. A surgical implant such as a stent endoprosthesis must be made of a non-toxic, biocompatible material in order to minimize the foreign-body response of the host tissue. The implant must also have sufficient structural strength, biostability, size, and durability to withstand the conditions and confinement in a body lumen.

All documents cited herein are incorporated herein by reference in their entireties for all purposes.

SUMMARY OF THE INVENTION

The therapeutic advantage of permanent metal stent implants may be lost after several years of implant residence time in the body. For example, stent occlusion may occur due to collapse of the stent, restenosis from chronic tissue hyperplasia, or plugging from the flow disturbances contributing to biofilm formation or thrombosis. Solid plastic tubular removable stents require an interventional procedure for removal, and dilators typically have to be used repeatedly in periodic interventions to be effective. The disadvantages of permanent metal expandable or solid plastic tubular removable stents are addressed in part by bioabsorbable stents, but bioabsorbable stents can have their own disadvantages.

Fast-absorbing bioabsorbable stents used as short-term implants necessarily release degradation products at a relatively rapid rate compared to slow-absorbing polymers for longer-term stents. The "burst" of degradation products from fast-absorbing stents can potentially cause significant inflammation and hyperplasia leading to obstruction or clinical complications. Slow-absorbing bioabsorbable stents may have acceptable tissue response during absorption, but these stents are present in the body for at least 12 months. In both the cases of fast- and slow-absorbing stents, the implants can break apart into large pieces at locations of high stress or strain when degradation occurs. Such large pieces can cause tissue damage, if the fracture surfaces are sharp, and may lead to luminal obstruction. Prostatic and esophageal stents of this type have had to have larger pieces removed. There are no temporary stents that do not require an invasive procedure for removal available on the market that behave like the expandable, long-term stents and that can be used as a bridge to adjuvant therapies.

Accordingly, there is provided according to the present invention disintegrating stents for use in a body lumen that are appropriate for short (up to six weeks), medium (from six weeks to six months) and long-term (over six months) implant residence time and that require no interventional procedure for removal. More specifically, the present invention relates to improved stents designed to undergo controlled, purposeful, and beneficial fracture and/or disintegration without the need for interventional removal, in the case of metal or other other biostable materials, or, in the case of bioabsorbable materials, prior to complete absorption or encapsulation of the stent within the vessel wall.

The invention also relates to mechanisms to promote fracture of the stent into small pieces or particles. In particular, the disintegrating stents of the present invention include mechanisms to cause the stents to break apart into small, soft pieces once they are no longer needed. The products of the disintegration of the stent are then harmlessly transported by vessel contents, for example, bile, urine, fecal matter, gastric contents, mucous and air, and eliminated by excretion or exhalation.

The disintegrating stent of the present invention is preferably made of the Wallstent design technology using bioabsorbable polymer monofilaments as described in U.S. patent application Ser. No. 08/904,467, filed Aug. 1, 1997, the specification of which is incorporated herein by reference in its entirety. Stent designs other than the Wallstent braided construction may also be used according to the present invention, such as a single helical coil, rolled film or sheet, knitted or woven filaments, or extruded tubes. The preferred materials are bioabsorbable polymers, because if some of the disintegration particles become entrapped in the body, they can safely undergo the full absorption process. Bioabsorbable polymer resins such as PLA, PLLA, PDLA, PGA and other bioabsorbable polymers are commercially available from several sources including PURAC America, Inc. of Lincolnshire, Ill.

While all bioabsorbable stents "disintegrate" during the absorption process, one object of the present invention is to purposely design the implant to cause fracture and/or disintegration to happen, preferably at specific sites and the pieces eliminated from the body, rather than rely on complete bioabsorbtion of the stent within the body. In particular, the invention relates to engineered biodegradation to promote predictable and designed fracture and/or disintegration of the stent so that small stent pieces may be transported out of the body, rather than relying on the full bioabsorbability of the material to allow complete dissolution of the stent.

While bioabsorbable materials are preferred according to the invention, it is envisioned that other materials, such as biostable polymers and metals may be used according to the invention whereby such stents weaken and fracture into fragments as a result of interaction with naturally occurring body chemicals with assistance from mechanical initiation sites.

The present invention may also be used to cause planned failure of solid plastic tubular biliary stents and other prosthetic surgical implants to make them temporary and self removing.

Methods of engineering planned stent disintegration and/or failure according to the present invention may include but are not limited to: controlling the formation of heterogeneous structure of amorphous and crystalline regions within the stent or stent filaments, creating multiple internal or surface fracture initiation sites, creating localized pre-degraded material, or using multiple strands with small section size to construct the stent. According to the invention, stent disintegration would occur at the initiation sites and the small particles would be transported by urine, bile, fecal matter, gastric contents, or air through the vessels to be excreted or exhaled from the body. Radiopaque agents could be mixed in with the polymer to add radiopacity to the stent.

The present invention also relates to manipulation of the molecular structure of a polycrystalline polymer and/or design of the material of an implant to purposely disintegrate such that the disintegration products become mobile in the vessel system and harmlessly pass out of the body prior to full-onset of the mass degradation process. Polycrystalline bioabsorbable polymers are known to have amorphous regions and crystalline regions. These polycrystalline bioabsorbable polymers are known to degrade preferentially in the amorphous regions first and then subsequently in the crystalline regions.

The conventional objective of materials and implant design engineers has been to control or manipulate the manufacturing process to avoid early disintegration from fast-degrading amorphous regions by trying to increase the crystallinity of the polymer. The result is that bioabsorbable stents of the prior art are comprised of polymer monofilaments that are generally 40%-60% crystalline. By contrast, the present invention relates to thermomechanically processing a bioabsorbable polymer to produce more fast-degrading amorphous regions in the material to create predictable and/or more numerous sites of polymer fragmentation. Amorphous regions may be created by fast cooling of melt-spun polymer extrudate to prevent nucleation and growth of significant crystalline regions.

The concentration and morphology of the fast-degrading amorphous regions and the mechanical stresses and strains in the implant determine the disintegration product size. According to the invention, the polymer material preferably comprises greater than 60% amorphous regions, or, stated another way, less than 40% crystallized regions. On the other hand, if the amorphous regions comprise too great a proportion of the polymer material, the strength of the monofilament may not be sufficient to survive the braiding process. Accordingly, the amorphous regions preferably do not comprise more than about 80% amorphous regions, or not less than about 20% crystallized regions. Hence, the amorphous regions preferably comprise about 60% to about 80% amorphous regions (corresponding to about 20% to about 40% crystallized regions) and more preferably, the amorphous regions may comprise between about 60% to about 70% (about 30% to about 40% crystallized regions). For some applications which have lower strength requirements for the stent, the amorphous regions may comprise from about 70% to about 80% of the polymer material (corresponding to about 20% to about 30% crystallized regions). The relative proportion of amorphous to crystallized regions may be determined by differential scanning calorimetry.

The degradation rate or manufactured physical and mechanical properties of the slow-degrading or more biostable regions, respectively, determine the physical and mechanical properties of the disintegration products. Preferably, the stents of the present invention are engineered so that the disintegration products are on the order of about 10 microns to one centimeter in size, preferably from about 0.1 mm to about 5 mm in size, more preferably from about 0.5 mm to about 2.5 mm in size and most preferably about 1 mm in size, and are relatively soft and blunt-edged, so that they are advantageous for safe, harmless passage through the vessels of the body.

Another method of creating multiple fracture initiation sites in a biodegradable polymer is to create periodic regions of pre-degraded material along a stent or a structural element of a stent, such as a monofilament. Post-extrusion or molding operations such as localized degradation of molecular weight of crystalline materials may be performed with lasers, focal UV light sources, water or steam hydrolysis, or irradiation. When the material is presented into an environment that provides heat and moisture for hydrolytic polymer degradation, the pre-degraded regions will lose strength and disintegrate sooner than regions of the material that were not pre-degraded. The frequency of occurrence of the pre-degraded regions will affect the size of the fracture pieces from disintegration. A low frequency of pre-degradation regions will result in disintegration into relatively large pieces. A high frequency will result in disintegration into relatively small pieces.

In addition to, or as an alternative to, manipulating the molecular structure, mechanical disintegration and/or fracture sites may be designed into the implant to cause predictable, controlled fracture and/or disintegration. Mechanical disintegration initiation sites may be created in the material or implant, for example, by purposely notching, grooving, indenting, or contouring the surface. Internal mechanical initiation sites may be created by purposely introducing porosity or foreign particles in the solidifying polymer.

Alternatively, unmodified bioabsorbable polymers may be used in the form of thin monofilaments or cable strands to construct the stent. Thinner monofilaments disintegrate into finer particles than the thicker (0.25 mm diameter) monofilaments. Thus, one embodiment of the invention relates to replacing the standard 24 single strands of 0.25 mm diameter bioabsorbable polymer monofilament with 24 paired strands of 0.12 mm diameter monofilament or, alternatively, 24 strands of pre-braided cable each containing two or more monofilaments of very fine diameter, about 0.05 mm or less in diameter. This embodiment of the present invention may also be extrapolated for use in large stents such as 22 mm diameter esophageal or colonic stents where large diameter monofilaments would traditionally be used in the braids. It is beneficial to control the disintegration particle size in these large stents by using multiple, small diameter filaments in their design so that the fragments are be less harmful and more easily passed through the vessel system out of the body.

Additionally, the disintegrating stents of the present invention may be designed so that they are strained by the body to promote disintegration at purposely created weak spots within the material. An example would be to significantly oversize all or portions of a self-expanding stent within a vessel. Prior to implantation the device would be unstrained. After delivery to and release within the target vessel, the stent may be strained, as a result of its larger size relative to the vessel diameter. This strain will facilitate fracture of the stent at the pre-manufactured weak spots after a pre-determined amount of time and the stent will break into small soft particles to be carried away by the vessel contents.

The disintegrating stent of the present invention may be positioned to serve as a bridge to surgery, bridge to radiation, or bridge to onset of drug therapy. The stent may also be used to hold issues in place while healing occurs, for example after traumatic injury or surgery. Stents intended for management of obstructed lumens may be made in this manner where the stent was only needed to be present for couple of weeks to a few months; e.g., for a bridge to adjuvant therapy or surgery.

Disintegrating stents of the present invention may be delivered to the target lumen using a Unistep Plus™ or other catheter type of delivery system. The stents may be implanted as are metal or bioabsorbable Wallstents.

The present invention may be used advantageously in connection with all manner of stents. A preferred embodiment of the invention relates to improved bioabsorbable stents. In particular, all features of the bioabsorbable stents described in U.S. patent application Ser. No. 08/904,467, filed Aug. 1, 1997, are considered by the inventors to be features of the present invention.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DESCRIPTION OF THE DRAWINGS

FIG. 1b' is a simplified representation of a braided tubular stent of the type illustrated in FIG. 1a;

FIG. 1b shows an alternative braid structure for the braided tubular bioabsorbable stent shown in FIGS. 1a and 1b';

FIG. 2 is a partial longitudinal cross-sectional view of the stent shown in FIG. 1a;

FIG. 3 is a cross-sectional view of one of the filaments of the stent shown in FIG. 1a;

DETAILED DESCRIPTION OF THE INVENTION

Figure 1A:
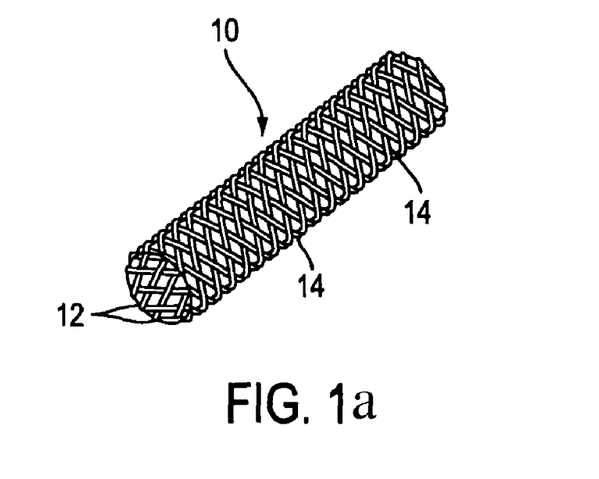
FIG. 1a is an isometric view of an example of a braided filament bioabsorbable stent, comprised of 0.25 mm single filament strands, that may be used in connection with the present invention.
Figure 2:
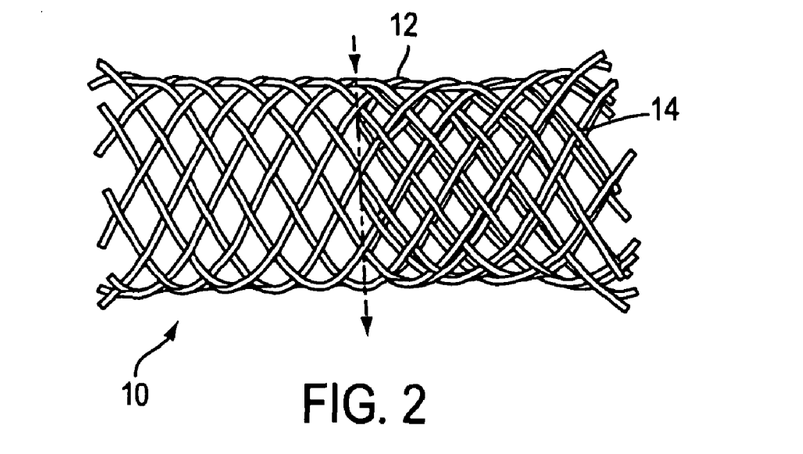
Figure 3:
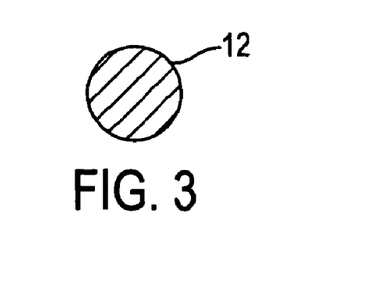
Figure 4:
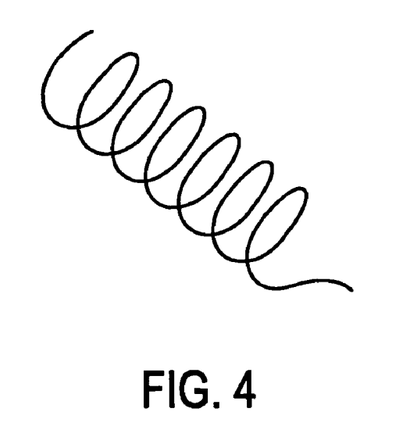
FIG. 4 is an isometric view of an example of a bioabsorbable stent comprised of a single helical coil of polymer monofilament that may be used in connection with the present invention.
Figure 5:
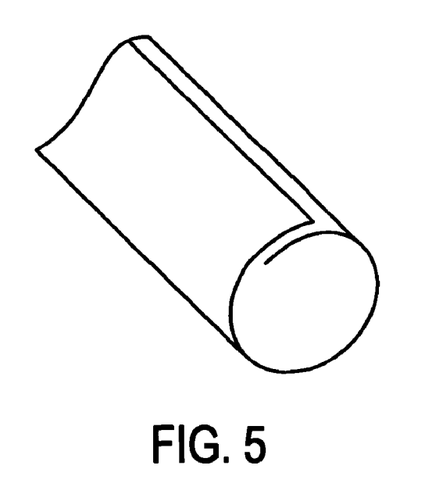
FIG. 5 is an isometric view of a rolled film or sheet-type bioabsorbable stent that may be used in connection with the present invention.
Figure 6:
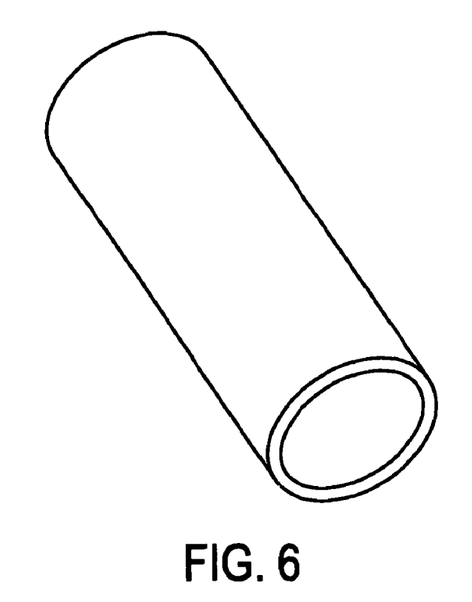
FIG. 6 is an isometric view of a solid extruded or molded tube-type bioabsorbable stent that may be used in connection with the present invention.
Figure 7:
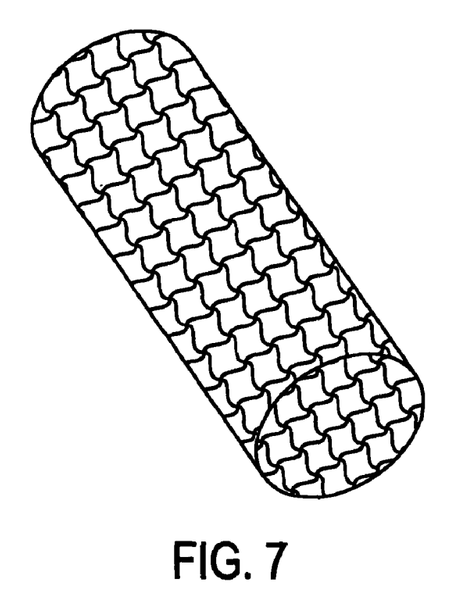
FIG. 7 is an isometric view of a knitted or woven polymer filament-type bioabsorbable stent that may be used in connection with the present invention.

An implantable prosthesis or stent 10 according to a preferred embodiment of the present invention is illustrated generally in FIGS. 1a and 2. FIG. 4 shows an alternative embodiment of the invention according to which the stent is comprised of a single helical coil of polymer monofilament. FIG. 5 shows an alternative embodiment of the invention according to which the stent is comprised of a rolled film or sheet. FIG. 6 shows an alternative embodiment of the invention according to which the stent is comprised of a solid extruded or molded tube. FIG. 7 shows an alternative embodiment of the invention according to which the stent is comprised of knitted or woven polymer filaments. Stents of the type illustrated in FIGS. 4-7 are generally well-known in the art and may be manufactured according to well-known methods. Any of the stents according to the embodiments of FIGS. 4-7 may be made using bioabsorbable or biostable materials.

Referring again to the preferred embodiment of FIGS. 1a and 2, stent 10 is a tubular device formed from two sets of oppositely-directed, parallel, spaced-apart and helically wound elongated strands or filaments 12. The stent of FIGS. 1a and 2 is described in more detail in U.S. patent application Ser. No. 08/904,967, filed Aug. 1, 1997. In particular, the sets of filaments 12 are interwoven in an over and under braided configuration intersecting at points such as 14 to form an open mesh or weave construction. According to one embodiment of the invention, at least one and preferably all filaments 12 consists of one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid) or related copolymers materials. Methods for fabricating stents 10 are generally known and disclosed, for example, in the Wallsten U.S. Pat. No. 4,655,771 and the Wallsten et al. U.S. Pat. No. 5,061,275.

Stent 10 is shown in its expanded or relaxed state in FIGS. 1a and 2, i.e., in the configuration it assumes when subject to no external loads or stresses. The filaments 12 are resilient, permitting the radial compression of stent 10 into a reduced-radius, extended-length configuration or state suitable for delivery to the desired placement or treatment site through a body vessel (i.e., transluminally). Stent 10 may also be self-expandable from the compressed state, and axially flexible.

According to one embodiment of the invention, stent 10 may be a radially and axially flexible tubular body having a predetermined diameter that is variable under axial movement of the ends of the body relative to each other. Stent 10 may be composed of a plurality of individually rigid but flexible and elastic thread elements or filaments 12, each of which may extend in a helix configuration along a longitudinal center line of the body as a common axis. The filaments 12 may define a radially self-expanding body. The body may be provided by a first number of filaments 12 having a common direction of winding but axially displaced relative to each other, and crossing a second number of filaments 12 also axially displaced relative to each other but having an opposite direction of winding.

Other structures and features may be included in the stents of the present invention, for example, stents having features which enhance or cooperate with the tubular and self-expandable structure or which facilitate the implantation of the structure. One example is the inclusion of radiopaque markers on the structure which are used to visualize the position of the stent through fluoroscopy during implantation. Other examples include collapsing threads or other structures to facilitate repositioning of the stent.

In the absence of designed controlled fracture, structural failure of stents can result in the breaking loose of large pieces which may damage tissue and/or lodge in and obstruct the lumen. Thus, the present invention is directed towards the design of stents that disintegrate with planned, controlled fracture into small soft fragments that may be easily carried away by body fluids and eliminated from the body.

Mechanisms for the planned controlled disintegration and/or fracture of stents according to the invention are described in the following examples with reference to FIGS. 10 through 14.

Example 1

One method of creating multiple fracture initiation sites in a biodegradable polymer is to create a structure having more amorphous and less crystalline regions in the material.

Methods for making polycrystalline monofilaments are generally known. For example, methods for making PLA monofilaments are described in detail in U.S. patent application Ser. No. 08/904,467, filed Aug. 1, 1997. Generally, PLA monofilaments may be produced by a process involving seven general steps as summarized herein. Methods of making monofilaments from other polycrystalline polymers, including but not limited to the polymers enumerated hereinabove, are equally well known to those of ordinary skill in the art, and this example is not intended to limit the present invention in any way.

First, a polymer formed of poly-L-lactic acid is brought to an elevated temperature above the melting point, preferably 210°-230° C. Second, the material is then extended at the elevated temperature into a continuous fiber, by a conventional process, at a rate about of three to four feet per minute. Third, the continuous fiber is then cooled to cause nucleation. The cooling is preferably performed by passing the fiber through a nucleation bath of water. Fourth, the material then passes through a first puller, which runs at about the same speed as the extruder, and places the material under slight tension. Fifth, the fiber is then heated to a temperature between about 60° C. and about 90° C. (preferably 70° C.) as it passes through a heated oven. To perform annealing, the oven can be designed to be quite long and heated near the end, so that the orientation and annealing take place in the same oven. Alternatively, a separate oven can be placed directly after the orientation oven. The annealing step heats the fibers to a range of about 65° C. to about 90° C., preferably closer to 90° C. Sixth, while being heated in the orientation oven and the annealing oven, the fiber is drawn between the first puller located before the orientation oven and a second puller located after the annealing oven (if a separate oven). The material is drawn at a draw ratio of between about 5 to about 9, preferably between about 6 and about 8. Draw ratio describes the extension in length resulting from polymer extrusion or drawing. Quantitatively, the drawing ratio is a unitless value equal to the extruded or drawn length divided by the original length. Maintaining tension through the annealing step prevents shrinkage in later use. The second puller, located at the exit of the oven, runs at an increased speed necessary to provide the desired draw ratio. As the fiber exits the oven and passes through the second puller the tension is immediately released before the material cools. Seventh, finally, the fiber is collected onto spools of desired lengths.

Degradation is known to occur faster in amorphous material than in crystalline material. Polycrystalline polymers are generally amorphous because of the material's slow crystallization kinetics. Previously, the goal of the stent engineer was to make the filaments as crystalline as possible. Very slow cooling after drawing of the filament or use of a nucleating agent will cause increased crystallization. Alternatively, the material can be annealed at temperatures above 60° C. to cause crystallization. However, according to the present invention, a more amorphous filament is desired, characterized by fewer regions of crystalline, oriented regions located among more numerous amorphous regions. Therefore, the amorphous regions act as initiation sites for fracture if the amorphous area is large enough to form a fissure or crack that can propagate through the section thickness of the material or to another fissure or crack.

Figure 8:
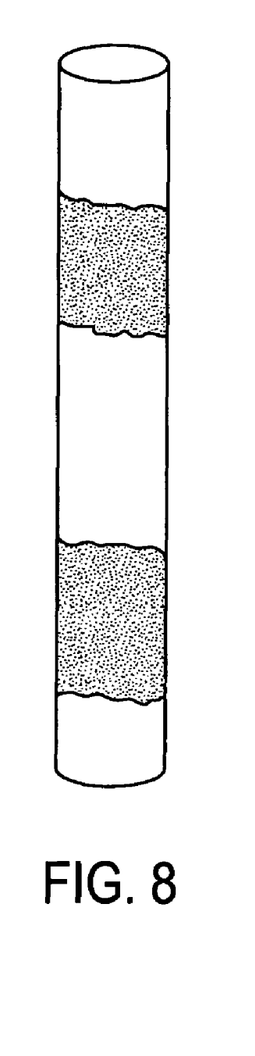
FIG. 8 is a representation of a polymer monofilament having bands of crystalline material separated by amorphous material.
Figure 9:
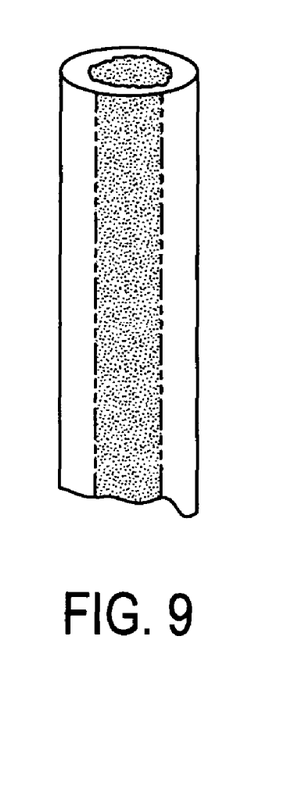
FIG. 9 is a representation of a polymer monofilament having a center core of more crystalline material and a surface of more amorphous material.
Figure 10:
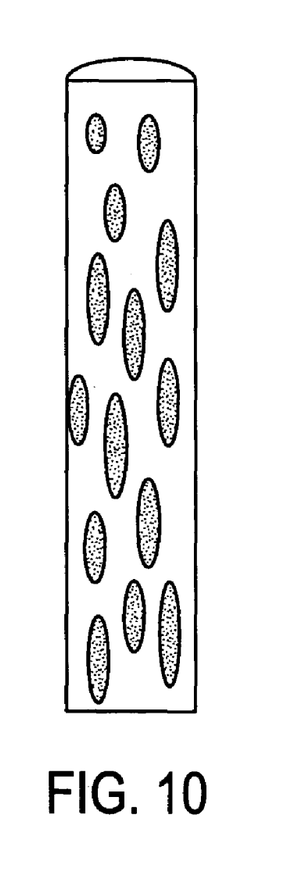
FIG. 10 is a representation of a polymer monofilament having a heterogeneous structure of crystalline and amorphous regions randomly dispersed throughout its cross-section.

The more amorphous structure can be created, for example, by controlling the solidification cooling rate of the polymer. Fast cooling prevents nucleation and growth of crystallites and slow cooling promotes crystallization. Polymer extrudate that is cooled quickly will have less crystallinity than a more slowly cooled extrudate. If the monofilament extrudate can be cooled along the length with alternating fast and slow cooling rates, a banded structure will form, FIG. 8. One method of doing this is pulsing the pull rate of the extrudate filament through the cooling bath after it exits the spinnerette. Another method is to use cooling jet nozzles directed at the extrudate and alternately pulse colder and warmer water as the material is being pulled past the nozzle. If the section size of the extrudate is large enough, a gradient of crystallinity can be created from surface to center. The center of the thickness will cool more slowly than the surface because of heat transfer kinetics. If the temperature gradient is sufficiently large, the center will be more crystalline than the material near the surface, FIG. 9. In use, the material near the surface will degrade more rapidly than the center, because it has more amorphous regions. Disintegration will occur by delamination of material near the surface from the more crystalline core. The remaining intact material in the core of the structural element will have reduced section size relative to the initial element (prior to degradation and disintegration of the surface), and in the end, it would disintegrate into smaller pieces than if the entire structural element were to have fractured at once. Uncontrolled crystallization occurs by nucleation and growth of crystallites in the cooling extrudate resulting in a structure comprising pockets of crystalline regions randomly dispersed in amorphous regions, FIG. 10. The difference between controlled and uncontrolled heterogeneity is illustrated in FIGS. 8-10.

The concentration and morphology of the fast-degrading amorphous regions directly relate to the disintegration product size. Accordingly, persons of ordinary skill in the art can easily vary the rate of cooling to adjust the relative proportion of amorphous regions and crystallized regions to achieve the desired disintegration product size, preferably small enough to easily be carried away by body fluids and eliminated.

Example 2

Mechanical properties generally increase with increasing molecular weight. For instance, the strength and modulus of polycrystalline polymers generally increase with increasing molecular weight. Conversely, degradation time generally decreases with decreasing initial molecular weight (i.e., a stent made of a low molecular weight polymer is bioabsorbed more quickly than a stent made of a high molecular weight polymer). Moreover, the molecular weight and mechanical properties of the material generally decreases as degradation progresses. Accordingly, in addition to, or as an alternative to, the creation of a heterogeneous molecular structure to promote controlled disintegration and fracture, the stent material may be subjected to post-extrusion or molding operations to create pre-selected "weak spots," localized pre-degradation of the molecular weight of the crystalline structure of the polymer.

Figure 11:
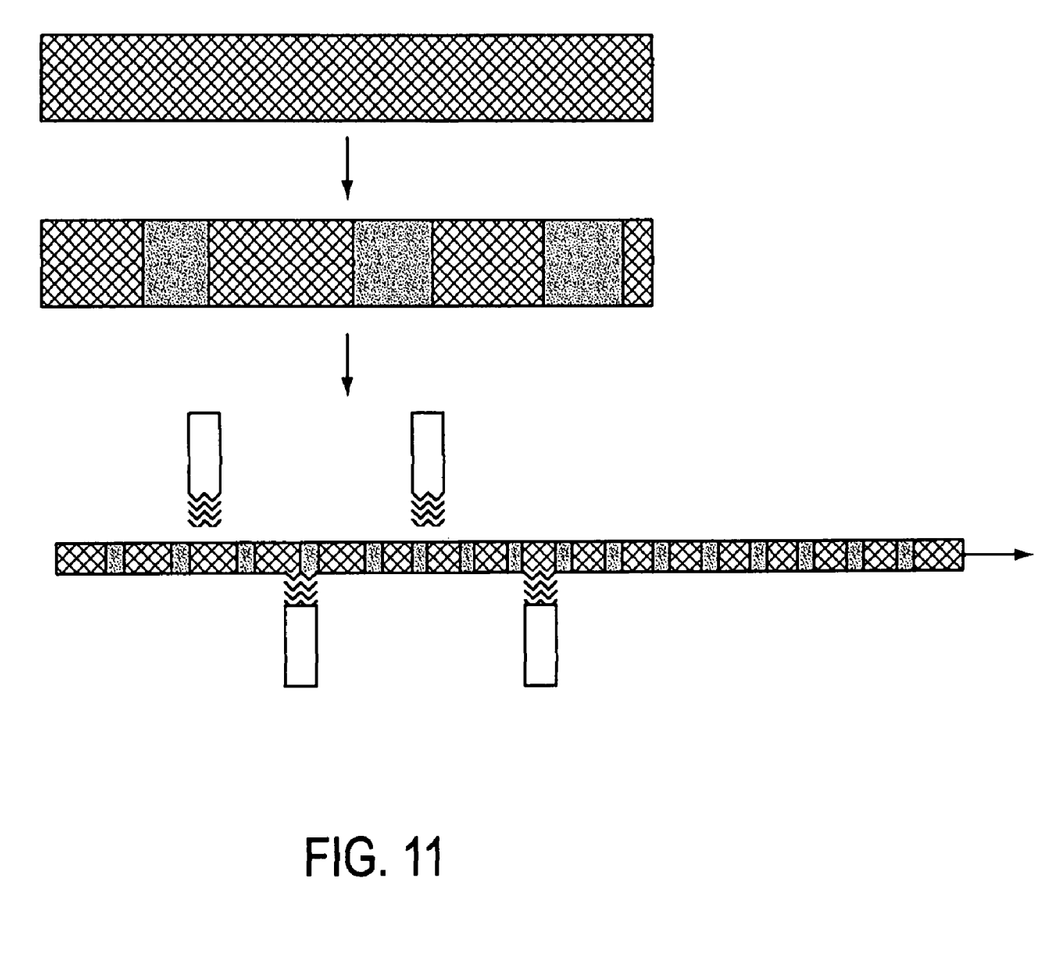
FIG. 11 is a representation of another embodiment of the invention according to which localized pre-degraded regions are created by exposure to heat, light, moisture or radiation.
Figure 12A:
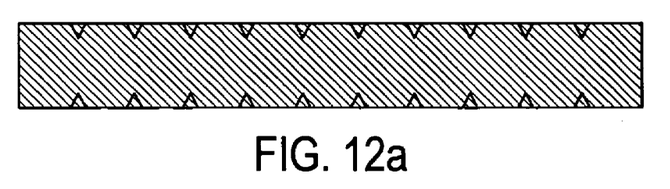
FIGS. 12a-12c are representations of further embodiments of the invention according to which surface initiation sites are created, for example, by notching, by grooving, or by indenting of the filament or stent surface.
Figure 12B:
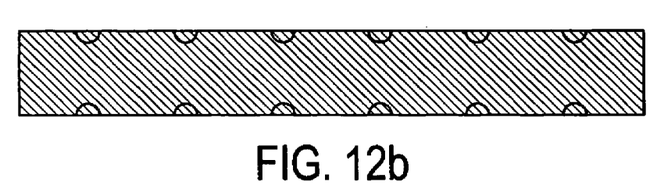
Figure 12C:
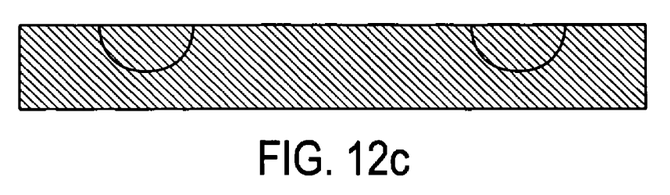
Figure 13:
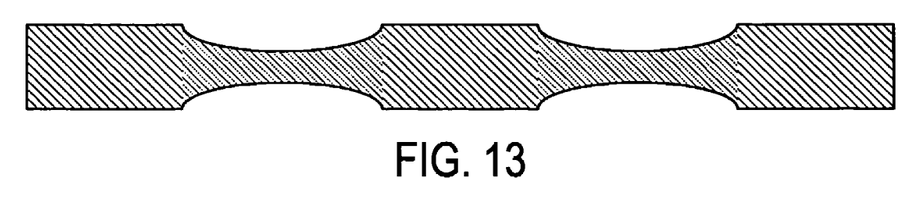
FIG. 13 is a representation of another embodiment of the invention according to which filaments are contoured to provide narrowed sections to facilitate controlled fracture.
Figure 14:
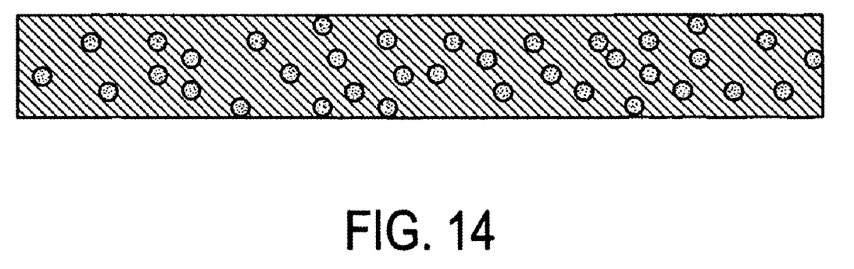
FIG. 14 is a representation of another embodiment of the invention according to which internal disintegration initiation sites are provided, for example by introducing pores, air pockets or foreign particles into the filament.

One method of creating pre-degraded regions in a monofilament is to mask some portion of the surface and expose the bare surface areas to treatments known to cause degradation in bioabsorbable polymers such as heat, light or other UV radiation, and heated water or steam, FIG. 11. According to this embodiment of the invention, a long length of braided bioabsorbable polymer monofilament stent is manufactured, and its surface is then masked with removable strips that are wrapped around the circumference of the stent. The stent is then passed through treatment nozzles to project heat, UV radiation, or heated water onto the surface. The rate of movement of the stent through the nozzles is set to allow sufficient residence time within the treatment medium to cause degradation of the bare polymer or repeated passes can be made. The maskant is then removed and the stent is cut into pieces of the finished design length and packaged for sterilization and subsequent medical use. Examples of treatment media would include quartz lamps or lasers to create heat, ultraviolet lamps to project UV radiation, and steam to supply heated moisture.

Example 3

In addition to manipulating the molecular structure during or after extrusion, mechanical features such as stress concentrations, fissures, notches grooves, indentations or surface contours may be designed into the implant to cause predictable, controlled fracture and/or disintegration. FIGS. 12*a-c* and 13 illustrate types of mechanical features may be introduced into the surfaces of stent materials to facilitate planned and controlled fracture.

Such periodic fracture initiation sites are designed such that they are not deleterious enough to initiate fracture in full-strength material. However, when degradation occurs and the material loses strength, the stress concentrations or fissures become more significant relative to the strength of the material and serve as points of weakness in the device in order to facilitate disintegration. The methods of making the features include lathe turning, milling, drilling, die-forming, laser curing, and chemical etching. Die chatter marks during polymer extrusion may also be advantageous for creating surface crack initiation sites. Usually die chatter is considered an undesirable aesthetic and structural feature. Larger, more pronounced surface features for initiating fracture upon degradation may be produced by localized stretching or die-forming to create a contoured profile in the filament. The contours may be transitions from full thickness to reduced thickness sections. The reduced thickness sections would have lower break loads and would preferentially fracture during degradation.

Example 4

According to yet another embodiment of the invention multiple initiation sites for fracture of the device into small pieces upon disintegration are created by internal porosity or discontinuities in the material. Internal porosity can be created, for example, by purposely causing gas entrapment within the polymer melt during melt extrusion. This may be done, for example, by purging the extrusion chamber with gas or by not applying sufficient vacuum to the chamber to evacuate all of the gas from the liquid polymer. Internal discontinuities may be created, for example, by blending the polymer resin with foreign particles. The particles may be biocompatible and may be dissolvable by the bodily fluids in which the device is to be implanted. If the device is to be implanted in the digestive system, the particles need not be bioabsorbable. They need only be small enough to not cause obstruction of the digestive tract. Examples of biocompatible particles that may be blended with the polymer resin include polymer microspheres (the polymer may be of the same material as the device and be hollow and/or they may be made from a different polymer material) and organic radiopaque agents such as barium sulfate and bismuth trioxide.

Example 5

Figure 1B:
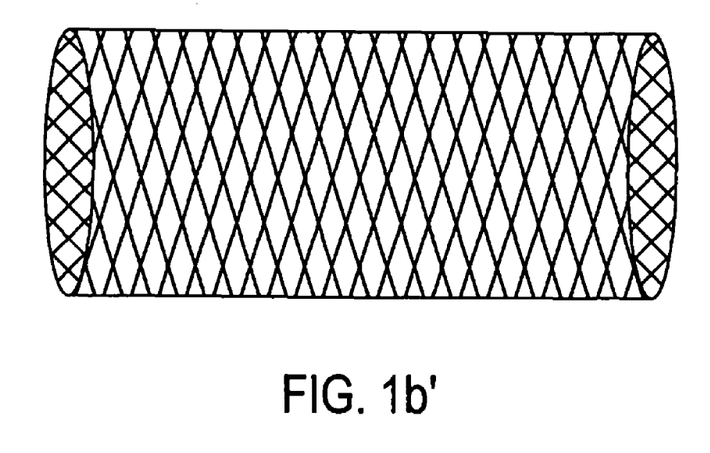
Figure 1C:
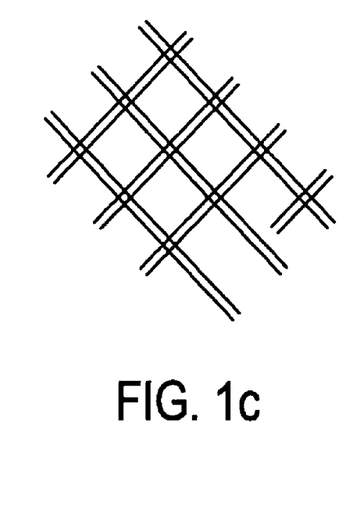
FIG. 1c shows a second alternative braid structure for the braided tubular bioabsorbable stent shown in FIGS. 1a and 1b' in which the stent is comprised of 0.12 mm paired filament strands.
Figure 1D:
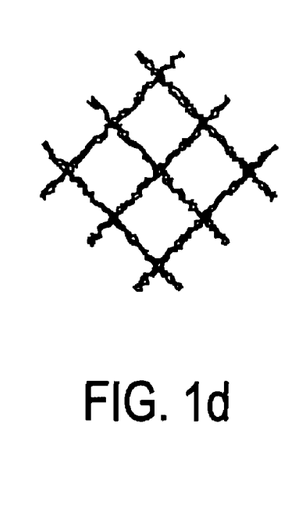
FIG. 1d shows a third alternative braid structure for the braided tubular bioabsorbable stent shown in FIGS. 1a and 1b' in which the stent is comprised of 0.25 mm (overall) cable strands.

According to an alternative embodiment of the invention, the filament structure of the stent may be modified to facilitate planned and controlled disintegration. According to this embodiment, optionally unmodified bioabsorbable polymers may be used in the form of thin monofilaments or cable strands to construct the stent. For example, instead of braiding a tubular stent from, for example, 24 single strands of 0.25 mm diameter bioabsorbable polymer monofilament as in FIG. 1*b* and described in U.S. patent application Ser. No. 08/904,467, the stent may be made from 24 paired strands of 0.12 mm diameter monofilament, FIG. 1*c*, or 24 strands of pre-braided cable each containing two or more monofilaments of very fine diameter, about 0.05 mm or less in diameter, FIG. 1*d*. According to this embodiment, the thinner monofilaments disintegrate into finer particles than the thicker (0.25 mm diameter) monofilament. Accordingly, if the filaments are otherwise unmodified, the entire stent disintegrates generally uniformly, but much more quickly and into smaller particle size as compared to stents made with filaments of larger diameter. Of course, if the smaller filaments of this embodiments are manufactured or treated according to any one or more of examples 1-3 herein, the disintegration and/or fracture will proceed accordingly.

Figure 15:
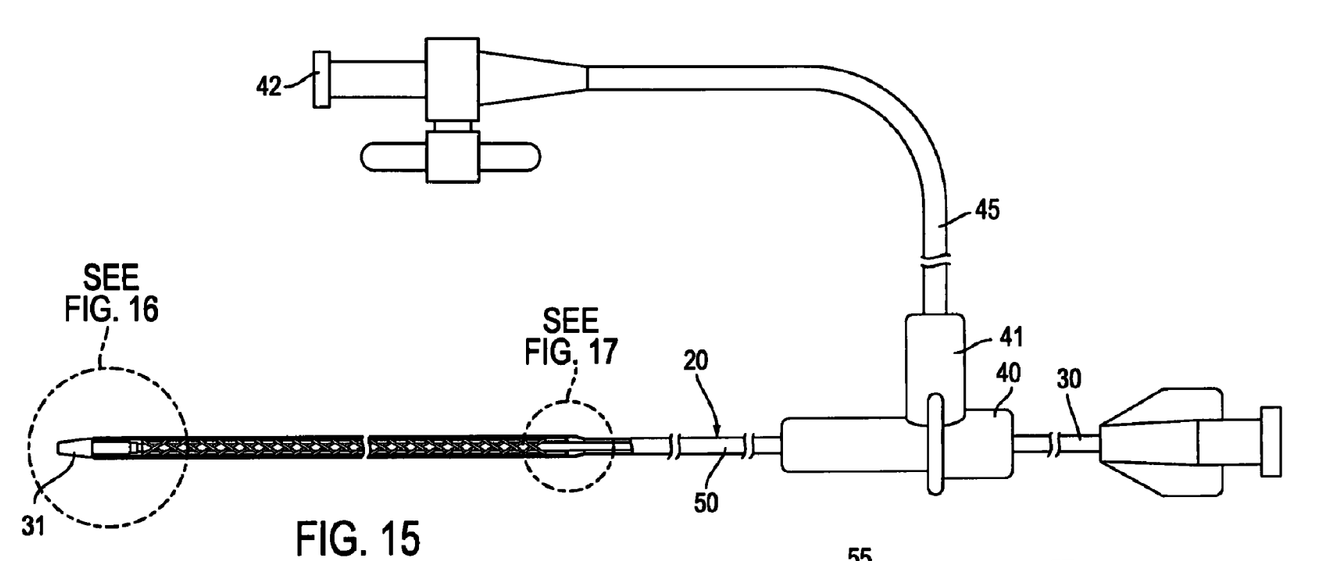
FIG. 15 is a side view of a delivery device with the stent shown in FIG. 1 loaded thereon.
Figure 16:
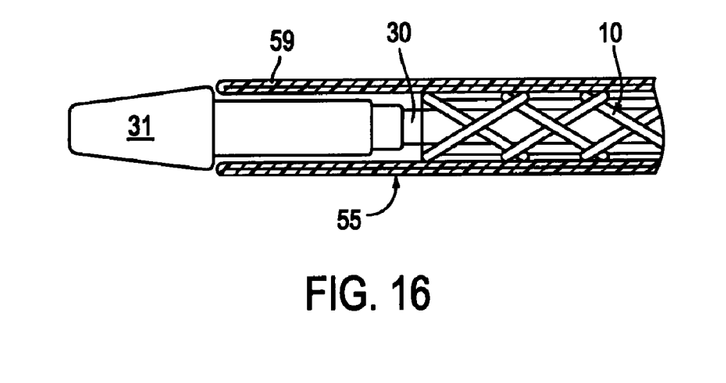
FIG. 16 is a detailed view of the portion of the delivery device encircled at "FIG. 16" in FIG. 15.
Figure 17:
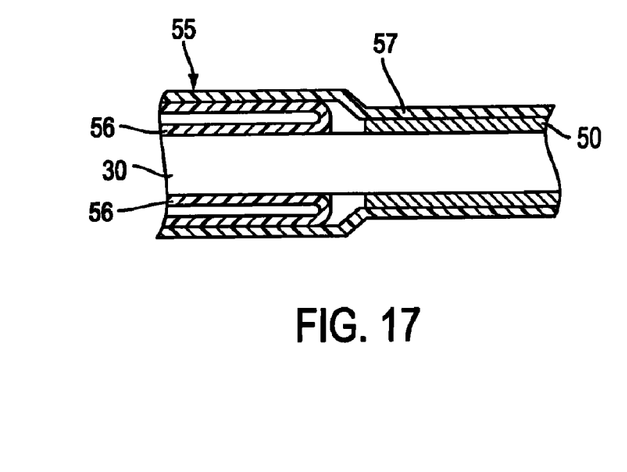
FIG. 17 is a detailed view of the portion of the delivery device encircled at "FIG. 17" in FIG. 15.
Figure 18:
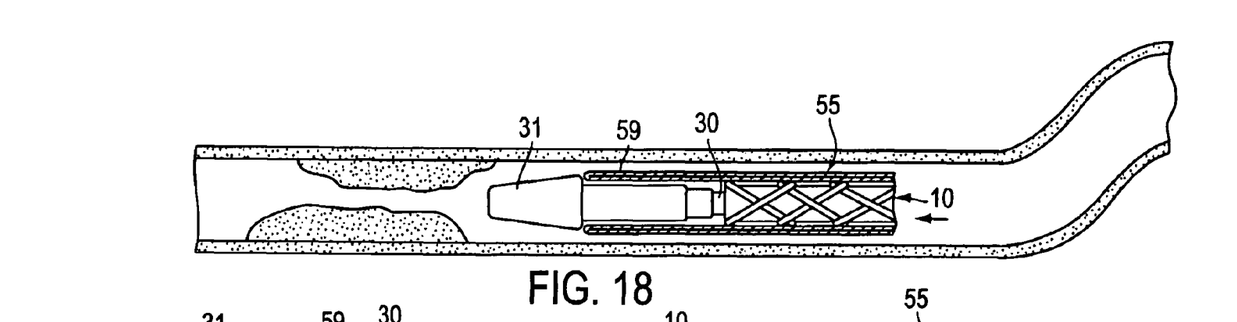
FIGS. 18-21 are partial cross-sectional side views of the distal portion of the delivery device and stent shown in FIG. 15 at various stages during a stent deployment operation in a body vessel.
Figure 19:
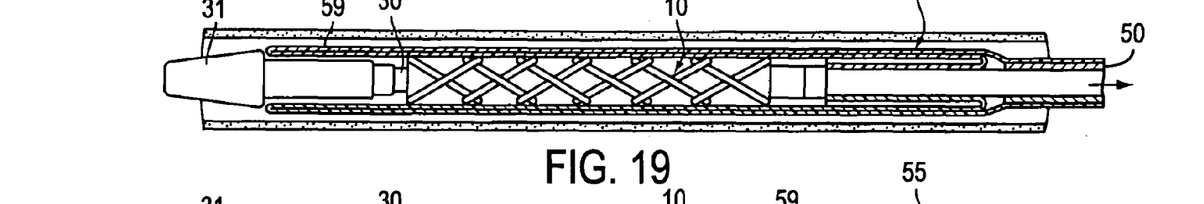
Figure 20:
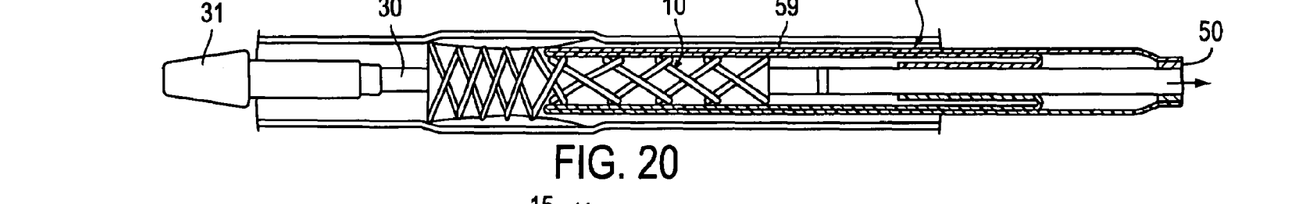
Figure 21:
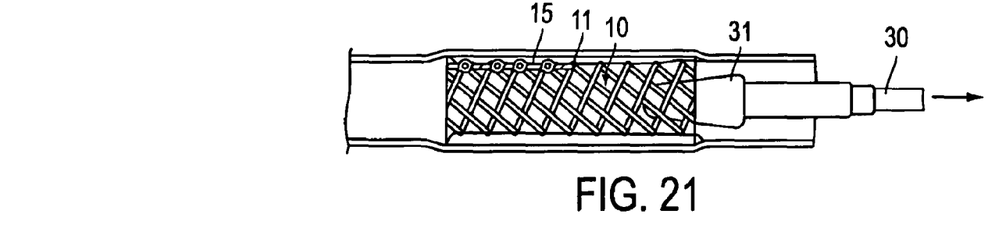
Figure 22:
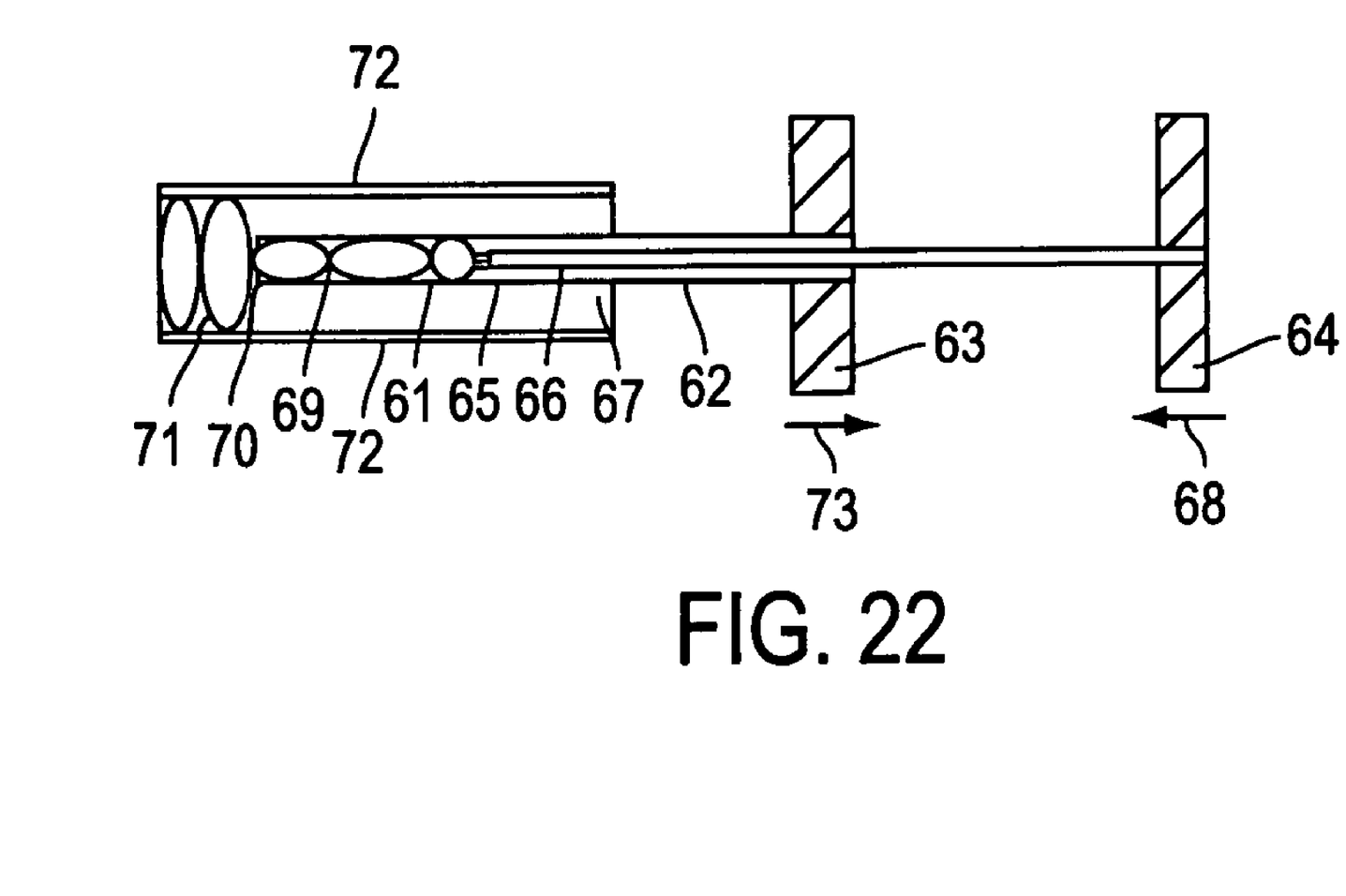
FIG. 22 is a side view of a pusher-type delivery device.

FIGS. 15-17 are illustrations of a coaxial inner/outer tube catheter delivery device 20 for delivering stent 10 to a treatment site in a body vessel.

As shown, stent 10 may be carried by the distal portion of delivery device 20, and is placed on the delivery device in a radially contracted or compressed state. The proximal portion of delivery device 20 generally remains outside of the body for manipulation by the operator.

The manner by which delivery device 20 is operated to deliver stent 10 to a treatment site in a body vessel or lumen including curved sections is illustrated in FIGS. 18-21. As shown, stent 10 is placed in a radially compressed state in a surrounding relationship to the outer distal end of inner tube 30. Stent 10 is constrained on inner tube 30 by the double-walled section of hose 55. It is important that stent 10 not be confined too tightly on inner tube 30. Hose 55 should apply just enough force to stent 10 to hold stent 10 in place. The double-walled section of hose 55 can be removed from around stent 10 by pulling valve body 40 and proximal tube 50 in a proximal direction. The double-walled section "rolls" off stent 10. No sliding movements take place between stent 10 and inner wall 56 which contacts stent 10. Along with the movement of the double-walled section in a proximal direction, the distal end of stent 10 will be exposed in a radial direction to engagement against the wall of the body vessel. As the double-walled section of hose 55 continues moving proximally, more of stent 10 expands in a radial direction until the entire length of stent 10 is exposed and engages the wall of a body vessel.

Lumen 35 is used to enable delivery device 20 to follow a guide wire (not shown) previously inserted percutaneously into the body vessel. The lumen of inner tube 30 can also be used to introduce a contrast fluid to the area around the distal end of delivery device 20 so the position of delivery device 20 can be detected (e.g., through the use fluoroscopy or X-ray techniques).

The stents of the present invention may be delivered by alternative methods or using alternative devices. For instance, the device described in Heyn et al. U.S. Pat. No. 5,201,757 may be utilized.

Figure 23:
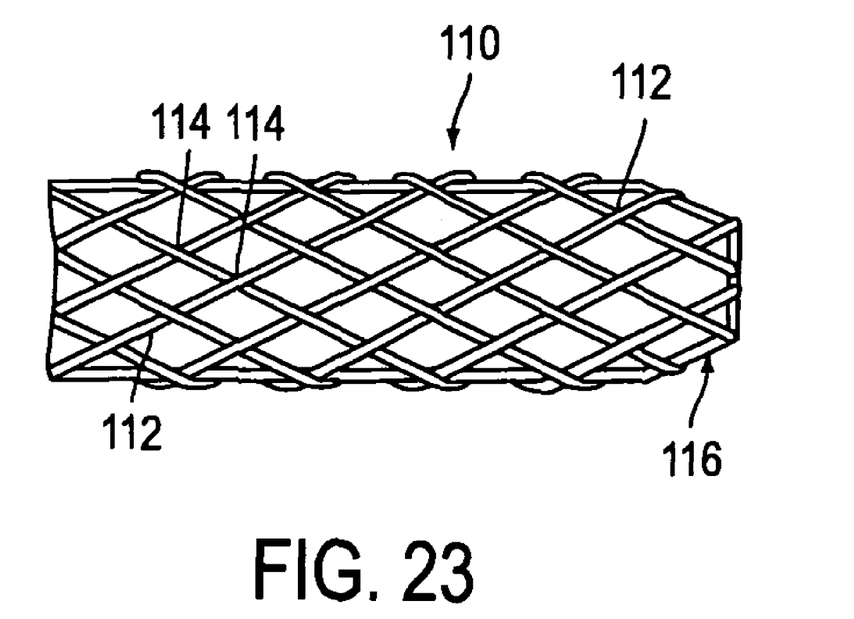
FIG. 23 is a side view of a second embodiment of a stent in accordance with the present invention.
Figure 24:
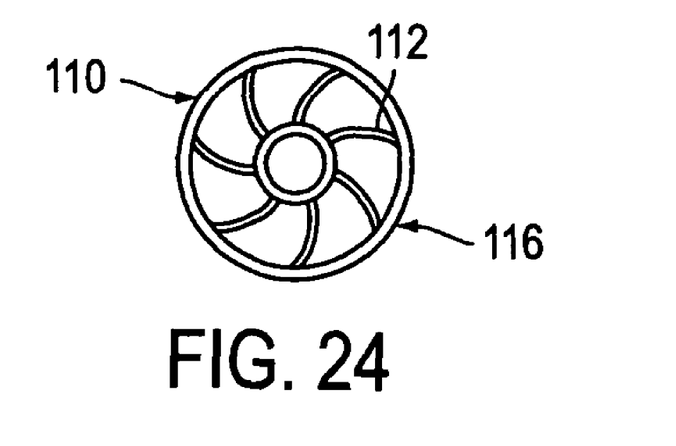
FIG. 24 is an end view of the stent shown in FIG. 23.

According to another embodiment of the present invention, illustrated in FIGS. 23 and 24, one end of the stent may be tapered. According to this embodiment, stent 110 is similar to stent 10 described above in that it is a tubular device formed from two sets of oppositely-directed, parallel, spaced-apart and helically wound elongated strands or filaments 112. The sets of filaments 112 are interwoven in an over and under braided configuration intersecting at points such as 114 to form an open mesh or weave construction. One end 116 of stent 110 is tapered and has a diameter which decreases from the diameter of the other portions of the stent to a reduced diameter. Stent 110 can be otherwise identical in structure and fabricated from the same PLLA or absorbable polymer materials as stent 10 described above. Stent 110 can be applied (in the manner of stent 10 described above) to a desired location within a vessel, for example, Vena Cava Inferior, for the purpose of preventing lung emboly. When used in this application, stent 110 can be inserted into Vena Cava with a high degree of precision and functions as a filter.

Although the present invention has been described with reference to preferred embodiments, those skilled in the art will recognize that changes can be made in form and detail without departing from the spirit and scope of the invention.

It will be evident from considerations of the foregoing that the devices of the present invention may be constructed using a number of methods and materials, in a wide variety of sizes and styles for the greater efficiency and convenience of a user.

The present invention relates to improved bioabsorbable stents. In particular, all features of the bioabsorbable stents described in U.S. patent application Ser. No. 08/904,467, filed Aug. 1, 1997, are considered by the inventors to be features of the present invention.

A bioabsorbable stent that may advantageously be used in conjunction with the present invention is disclosed in J. Stinson's U.S. patent application entitled "Bioabsorbable Self Expanding Stent", Ser. No. 08/904,467, filed Aug. 7, 1997, and commonly assigned to the assignee of this application.

Another bioabsorbable stent that may advantageously be used in conjunction with the present invention is disclosed in J. Stinson's U.S. Pat. No. 5,980,564 entitled "Bioabsorbable Implantable Endoprosthesis With Reservoir And Method Of Using Same", and commonly assigned to the assignee of this application.

Another bioabsorbable marker that may advantageously be used in conjunction with the present invention is disclosed in J. Stinson's and Claude Clerc's U.S. patent application entitled "Radiopaque Markers And Methods Of Using Same", Ser. No. 08/905,821, filed Aug. 1, 1997, and commonly assigned to the assignee of this application.

Another bioabsorbable marker that may advantageously be used in conjunction with the present invention is disclosed in J. Stinson's U.S. States patent application entitled "Bioabsorbable Marker Having Radiopaque Constituents And Method Of Using Same", Ser. No. 08/904,951, filed Aug. 1, 1997, and commonly assigned to the assignee of this application.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A method of using an implantable endoprosthesis comprising:
providing a tubular endoprosthesis structure for implantation into a body lumen of a patient's body, wherein the structure is radially compressible and axially flexible, the tubular endoprosthesis structure having a first diameter and comprising at least one filament having a nominal diameter wherein (i) the tubular endoprosthesis structure is notched, grooved or indented such that controlled fracture initiation sites are spaced apart along a length thereof or (ii) the at least one filament comprises a plurality of monofilaments having a diameter smaller than the nominal diameter wherein the plurality of monofilaments are notched, grooved or indented such that controlled fracture initiation sites are spaced apart along a length thereof to facilitate controlled disintegration of the tubular endoprosthesis structure;
disposing the tubular endoprosthesis structure into a delivery system at a second diameter that is smaller than the first diameter;
inserting the delivery system with the tubular endoprosthesis structure in a body lumen;
deploying the tubular endoprosthesis structure from the delivery system into the body lumen where the tubular endoprosthesis structure assumes a third diameter that is smaller than the first diameter; and
disintegrating the tubular endoprosthesis structure by fracturing the tubular endoprosthesis structure at the controlled fracture initiation sites into mobile disintegration products on the order of about 10 µm to 1 cm in length, thereby permitting the mobile disintegration products to be transported through the body lumen and eliminated from the body.

2. A method of using an implantable endoprosthesis according to claim 1, comprising the additional step of allowing the tubular endoprosthesis structure, that also is self-expandable, to self expand in the body lumen to a fourth diameter greater than the third diameter.

3. A method of using an implantable endoprosthesis according to claim 1, comprising the additional step of balloon expanding the tubular endoprosthesis structure in the body lumen to a fourth diameter greater than the third diameter.

4. The method of claim 1 wherein said tubular endoprosthesis structure further comprises collapsing threads.

5. The method of claim 1 wherein the tubular endoprosthesis structure is selected from the group consisting of braided stents, helical stents, and knitted or woven stents.

6. The method of claim 1 wherein said tubular endoprosthesis structure comprises from about 10 to about 30 filaments consisting essentially of poly (alpha-hydroxy acid) each having an average diameter from about 0.15 mm to about 0.60 mm, wherein said filaments are braided at a braid angle of from about 120 degrees to about 150 degrees on a braid mandrel of from about 3 mm to about 30 mm diameter.

7. The method of claim 6 further including the step of scoring at least one of said filaments to create controlled fracture initiation sites at spaced apart locations on the surface of the tubular endoprosthesis structure.

8. The method of claim 1, wherein said tubular endoprosthesis structure is scored to create controlled fracture initiation sites.

9. The method of claim 1 wherein at least one filament or a surface of the tubular endoprosthesis structure is notched, grooved or indented.

10. The method of claim 1 wherein at least one filament has a contoured surface with narrowed sections.

11. The method of claim 1 wherein the at least one filament comprises a plurality of monofilaments having a diameter smaller than the nominal diameter.

12. The method of claim 1, wherein the plurality of monofilaments have a diameter of about 0.05 mm or less.

13. The method of claim 1, wherein the tubular endoprosthesis structure is formed from bioabsorbable materials.

14. The method of claim 1, wherein the tubular endoprosthesis structure has an implant residence time of up to 6 weeks.

15. The method of claim 1, wherein the tubular endoprosthesis structure comprises a biostable material.

16. The method of claim 1, wherein the tubular endoprosthesis structure comprises a metal.

17. The method of claim 1, wherein the disintegration products are on the order of about 0.1 mm to about 5 mm in length.

18. A method for treating a patient at a site within a vessel, the method comprising:
providing a biocompatible medical device for implantation into a body lumen of a patient's body, wherein the device is comprised of a tubular structure that is radially compressible and axially flexible, the biocompatible medical device having a first diameter and comprising at least one filament having a nominal diameter wherein (i) the biocompatible medical device is notched, grooved or indented such that controlled fracture initiation sites are spaced apart along a length thereof or (ii) the at least one filament comprises a plurality of monofilaments having a diameter smaller than the nominal diameter wherein the plurality of monofilaments are notched, grooved or indented such that controlled fracture initiation sites are spaced apart along a length thereof to facilitate controlled disintegration of the biocompatible medical device;

providing a delivery system with the biocompatible medical device positioned on a portion of the delivery system in a compressed state at a second diameter that is smaller than the first diameter;

inserting the portion of the delivery system with the biocompatible medical device into the vessel at a location spaced from a treatment site, and manipulating the delivery system to advance the biocompatible medical device through the vessel to the treatment site;

deploying the biocompatible medical device from the delivery system where the biocompatible medical device assumes a third diameter that is smaller than the first diameter;

removing the delivery system from the vessel with the biocompatible medical device remaining in and supporting the vessel; and disintegrating the biocompatible medical device by fracturing the biocompatible medical device at the controlled fracture initiation sites into mobile disintegration products on the order of about 10 μm to 1 cm in length, thereby permitting the mobile disintegration products to be transported through the body lumen and eliminated from the body.

19. The method of claim 18 wherein said biocompatible medical device further comprises collapsing threads.

20. The method of claim 18 wherein said biocompatible medical device is selected from the group consisting of braided stents, helical coil stents, and knitted or woven stents.

21. The method of claim 18 wherein at least one filament or a surface of the biocompatible medical device is notched, grooved or indented.

22. The method of claim 18 wherein at least one filament has a contoured surface with narrowed sections.

23. The method of claim 18 wherein the at least one filament comprises a plurality of monofilaments having a diameter smaller than the nominal diameter.

24. The method of claim 18, wherein the plurality of monofilaments have a diameter of about 0.05 mm or less.

25. The method of claim 18, wherein the biocompatible medical device is formed from bioabsorbable materials.

26. The method of claim 18, wherein the biocompatible medical device has an implant residence time of up to 6 weeks.

27. The method of claim 18, wherein the biocompatible medical device comprises a biostable material.

28. The method of claim 18, wherein the biocompatible medical device comprises a metal.

29. The method of claim 18, wherein the disintegration products are on the order of about 0.1 mm to about 5 mm in length.

* * * * *